US006780880B1

(12) United States Patent
Whittle et al.

(10) Patent No.: US 6,780,880 B1
(45) Date of Patent: *Aug. 24, 2004

(54) FT-RAMAN SPECTROSCOPIC MEASUREMENT

(76) Inventors: Robert R. Whittle, 5006 Pine Needles Dr., Wilmington, NC (US) 28403; Frederick D. Sancilio, 2332 Ocean Point Dr., Wilmington, NC (US) 28405; Grayson Walker Stowell, 710 Darwin Dr., Wilmington, NC (US) 28405

( * ) Notice: Subject to any disclaimer, the term of this patent is extended or adjusted under 35 U.S.C. 154(b) by 198 days.

This patent is subject to a terminal disclaimer.

(21) Appl. No.: 09/649,447

(22) Filed: Aug. 25, 2000

Related U.S. Application Data (60) Provisional application No. 60/150,878, filed on Aug. 26, 1999.

(51) Int. Cl.[7] .............................................. A61K 31/44
(52) U.S. Cl. .......................................................... 514/338
(58) Field of Search .......................................... 514/338

(56) References Cited

U.S. PATENT DOCUMENTS

| | | | |
|---|---|---|---|
| 4,128,658 A | 12/1978 | Price et al. ................. | 424/285 |
| 4,255,431 A | 3/1981 | Junggren et al. ........... | 424/263 |
| 4,279,819 A | 7/1981 | Price et al. ........... | 260/326.5 S |
| 4,337,257 A | 6/1982 | Junggren et al. ........... | 424/263 |
| 4,508,905 A | 4/1985 | Junggren et al. ........... | 546/271 |
| 4,555,518 A | 11/1985 | Rainer ....................... | 514/338 |
| 4,596,795 A | 6/1986 | Pitha .......................... | 514/58 |
| 4,612,378 A | 9/1986 | Bosshard et al. ........... | 548/170 |
| 4,620,008 A | 10/1986 | Brändström et al. ........ | 546/271 |
| 4,628,098 A | 12/1986 | Nohara et al. ............... | 546/271 |
| 4,636,499 A | 1/1987 | Brändström et al. ........ | 514/222 |
| 4,725,691 A | 2/1988 | Brändström et al. ........ | 546/172 |
| 4,727,064 A | 2/1988 | Pitha .......................... | 514/58 |
| 4,738,974 A | 4/1988 | Brändström .................. | 514/338 |
| 4,753,955 A | 6/1988 | Matsuishi et al. ........... | 514/338 |
| 4,772,619 A | 9/1988 | Adelstein et al. ........... | 514/338 |
| 4,777,172 A | 10/1988 | Ife et al. .................. | 514/234.5 |
| 4,786,505 A | 11/1988 | Lovgren et al. ............. | 424/468 |
| 4,808,596 A | 2/1989 | Matsuishi et al. .......... | 514/303 |
| 4,820,708 A | 4/1989 | Ife et al. .................. | 514/232.8 |
| 4,840,799 A | 6/1989 | Appelgren et al. ......... | 424/493 |
| 4,853,230 A | 8/1989 | Lovgren et al. ............. | 424/466 |
| 5,021,443 A | 6/1991 | Bru-Magniez et al. ...... | 514/394 |
| 5,039,806 A | 8/1991 | Brändström et al. ........ | 546/271 |
| 5,045,321 A | 9/1991 | Makino et al. .............. | 424/475 |
| 5,070,101 A | 12/1991 | Kaminski .................... | 514/399 |
| 5,075,323 A | 12/1991 | Fain et al. ................... | 514/338 |
| 5,093,132 A | 3/1992 | Makino et al. .............. | 424/475 |
| 5,093,342 A | 3/1992 | Tomoi et al. ............... | 514/328 |
| 5,096,893 A | 3/1992 | Pitha et al. .................... | 514/58 |
| 5,106,863 A | 4/1992 | Hajos et al. ................. | 514/395 |
| 5,124,158 A | 6/1992 | Ruwart et al. .............. | 424/449 |
| 5,178,867 A | 1/1993 | Guittard et al. ............. | 424/473 |
| 5,196,205 A | 3/1993 | Borody ....................... | 424/653 |
| 5,204,118 A | 4/1993 | Goldman et al. ........... | 424/489 |

(List continued on next page.)

FOREIGN PATENT DOCUMENTS

| | | | | |
|---|---|---|---|---|
| DE | 4035455 A1 | 5/1992 | ......... | C07D/401/12 |
| EP | 0005129 A1 | 4/1979 | ......... | C07D/403/12 |
| EP | 0124495 A2 | 11/1984 | ......... | C07D/401/12 |
| EP | 0166287 B1 | 1/1986 | ......... | C07D/401/12 |
| EP | 0171372 A1 | 2/1986 | ......... | C07D/513/14 |
| EP | 0197013 A1 | 10/1986 | ......... | C07D/401/12 |
| EP | 0484265 A1 | 5/1992 | ......... | C07D/401/12 |
| EP | 0585722 A1 | 3/1994 | .......... | A61K/31/44 |
| EP | 0818674 A2 | 1/1998 | .......... | G01N/21/65 |
| JP | 61007281 A2 | 1/1986 | ......... | C07D/513/14 |
| JP | 61205211 | 9/1986 | .......... | A61K/31/44 |
| JP | 61271259 | 12/1986 | ........... | C07C/93/14 |
| JP | 02049774 A2 | 2/1990 | ......... | C07D/235/28 |
| JP | 06096581 | 4/1994 | ......... | G11C/114/01 |
| JP | 06316573 | 11/1994 | ......... | C07D/401/12 |
| WO | WO 89/03829 | 5/1989 | ......... | C07D/401/12 |
| WO | WO 92/08716 | 5/1992 | ......... | C07D/401/12 |
| WO | WO 93/21920 | 11/1993 | .......... | A61K/31/44 |
| WO | WO 94/02141 | 2/1994 | .......... | A61K/31/44 |
| WO | WO 94/27988 | 12/1994 | ......... | C07D/401/12 |
| WO | WO 95/01783 | 1/1995 | ............ | A61K/9/24 |
| WO | WO 95/01977 | 1/1995 | ......... | C07D/401/12 |
| WO | WO 95/18612 | 7/1995 | .......... | A61K/31/44 |
| WO | WO 95/32957 | 12/1995 | ......... | C07D/401/12 |
| WO | WO96/01622 | 1/1996 | ............ | A61K/9/24 |
| WO | WO 96/01623 | 1/1996 | ............ | A61K/9/26 |
| WO | WO 96/02535 | 2/1997 | ......... | C07D/401/12 |
| WO | WO 97/20851 | 6/1997 | ............. | C07F/7/08 |
| WO | WO 97/25030 | 7/1997 | ............ | A61K/9/46 |
| WO | WO 98/19668 | 5/1998 | ............ | A61K/9/50 |
| WO | WO 98/53803 | 12/1998 | ............ | A61K/9/28 |
| WO | WO 98/54171 | 12/1998 | ......... | C07D/401/12 |
| WO | WO 99/08500 | 2/1999 | | |

OTHER PUBLICATIONS

Tensmeyer et al.; "Analytical Applications of Raman Spectroscopy in the Pharmaceutical Field," *Trends in Analytical Chemistry* 8:1 19–24 (Jan. 1989).

International Search Report, PCT/US 00/ 23368, Date of Mailing: Jan. 2, 2001.

U.S. patent application No. 09/645,146 to Whittle et al. entitled *Dry Blend Pharmaceutical Formulations*; filed Aug. 24, 2000.

U.S. patent application No. 09/645,148 to Whittle et al. entitled *Dry Blend Pharmaceutical Unit Dosage Form*; filed Aug. 24, 2000.

(List continued on next page.)

*Primary Examiner*—James H. Reamer
(74) *Attorney, Agent, or Firm*—Myers Bigel Sibley & Sajovec, PA (57) ABSTRACT

Fourier Transform Raman Spectroscopy (FT-Raman) determines the isomer ratio of chemical compositions.

4 Claims, 3 Drawing Sheets

U.S. PATENT DOCUMENTS

| | | |
|---|---|---|
| 5,206,025 A | 4/1993 | Courteille et al. .......... 424/439 |
| 5,219,870 A | 6/1993 | Kim ........................... 514/338 |
| 5,232,706 A | 8/1993 | Palomo Coll ............... 424/475 |
| 5,244,670 A | 9/1993 | Upson et al. ................ 424/439 |
| 5,246,714 A | 9/1993 | Dahlinder et al. .......... 424/497 |
| 5,288,506 A | 2/1994 | Spickett et al. ............. 424/498 |
| 5,294,439 A | 3/1994 | Yamasaka et al. ....... 424/78.01 |
| 5,294,629 A | 3/1994 | Machinami et al. ........ 514/366 |
| 5,304,540 A | 4/1994 | Blackburn et al. ............. 514/2 |
| 5,352,688 A | 10/1994 | Kaminski ................... 514/357 |
| 5,362,424 A | 11/1994 | Lee et al. ..................... 264/4.3 |
| 5,374,730 A | 12/1994 | Slemon et al. .............. 546/271 |
| 5,385,739 A | 1/1995 | Debregeas et al. ......... 424/494 |
| 5,386,032 A | 1/1995 | Brändström ................ 546/271 |
| 5,391,752 A | 2/1995 | Hoerrner et al. ............ 546/271 |
| 5,399,700 A | 3/1995 | Min et al. .................... 546/271 |
| 5,417,980 A | 5/1995 | Goldman et al. ............ 424/464 |
| 5,433,959 A | 7/1995 | Makino et al. .............. 424/475 |
| 5,457,260 A | 10/1995 | Holt ............................. 585/820 |
| 5,476,669 A | 12/1995 | Borody ........................ 424/653 |
| 5,508,041 A | 4/1996 | Lee et al. ..................... 424/451 |
| 5,514,660 A | 5/1996 | Zopf et al. ..................... 514/25 |
| 5,518,730 A | 5/1996 | Fuisz .......................... 424/426 |
| 5,536,735 A | 7/1996 | Takechi et al. .............. 514/338 |
| 5,569,808 A | 10/1996 | Cansell et al. .............. 585/800 |
| 5,571,811 A | 11/1996 | Heeres et al. ................ 514/252 |
| 5,578,732 A | 11/1996 | Kato et al. ............... 546/273.7 |
| 5,582,837 A | 12/1996 | Shell ........................... 424/451 |
| 5,589,491 A | 12/1996 | Nakanishi et al. .......... 514/338 |
| 5,599,794 A | 2/1997 | Eek et al. ...................... 514/29 |
| 5,616,593 A | 4/1997 | Patel et al. .................. 514/321 |
| 5,620,964 A | 4/1997 | Roth et al. .................... 514/53 |
| 5,622,717 A | 4/1997 | Fuisz .......................... 424/488 |
| 5,629,305 A | 5/1997 | Eek et al. .................... 514/199 |
| 5,633,244 A | 5/1997 | Eek et al. .................... 514/199 |
| 5,635,520 A | 6/1997 | Uda ............................. 514/338 |
| 5,637,592 A | 6/1997 | Heeres et al. ................ 514/252 |
| 5,639,478 A | 6/1997 | Makino et al. .............. 424/475 |
| 5,639,754 A | 6/1997 | Heeres et al. ................ 514/252 |
| 5,650,411 A | 7/1997 | Heeres et al. ................ 514/252 |
| 5,651,987 A | 7/1997 | Fuisz .......................... 424/488 |
| 5,652,653 A | 7/1997 | Alsmeyer et al. ........... 356/301 |
| 5,656,286 A | 8/1997 | Miranda et al. ............. 424/469 |
| 5,665,730 A | 9/1997 | Senn-Bilfinger et al. .... 514/300 |
| 5,684,580 A | 11/1997 | Cooper et al. ............... 356/301 |
| 5,686,588 A | 11/1997 | Yoo .......................... 536/13.3 |
| 5,693,818 A | 12/1997 | Von Unge ............... 546/273.7 |
| 5,710,156 A | 1/1998 | Heeres et al. ................ 514/255 |
| 5,712,165 A | 1/1998 | Alvarez et al. ................ 436/21 |
| 5,714,504 A | 2/1998 | Lindberg et al. ............ 514/338 |
| 5,719,161 A | 2/1998 | Rainer ......................... 514/300 |
| 5,728,700 A | 3/1998 | Heeres et al. ................ 514/252 |
| 5,731,002 A | 3/1998 | Olovson et al. ............. 424/484 |
| 5,751,415 A | 5/1998 | Smith et al. ................. 356/301 |
| 5,753,630 A | 5/1998 | Zopf et al. ..................... 514/25 |
| 5,766,622 A | 6/1998 | Nelson ........................ 424/440 |
| 5,776,765 A | 7/1998 | Graham et al. .............. 435/280 |
| 5,811,426 A | 9/1998 | Heeres et al. ................ 514/252 |
| 5,811,547 A | 9/1998 | Nakamichi et al. ......... 540/589 |
| 5,817,338 A | 10/1998 | Bergstrand et al. ......... 424/468 |
| 5,840,552 A | 11/1998 | Holt et al. ................... 435/118 |
| 5,846,562 A | 12/1998 | Yanai et al. ................. 424/451 |
| 5,850,623 A | 12/1998 | Carman, Jr. et al. .......... 702/28 |
| 5,859,030 A | 1/1999 | Kohl et al. .................. 514/338 |
| 5,877,192 A | 3/1999 | Lindberg et al. ............ 514/338 |
| 5,912,179 A | 6/1999 | Alvarez et al. ................ 436/63 |
| 5,916,904 A | 6/1999 | Sato et al. ................... 514/338 |
| 5,929,244 A | 7/1999 | Von Unge ............... 546/273.7 |
| 5,948,789 A | 9/1999 | Larsson et al. .............. 514/299 |
| 5,982,484 A | 11/1999 | Clarke et al. ................ 356/301 |
| 6,100,975 A | 8/2000 | Smith et al. ................. 356/301 |
| 6,150,380 A | 11/2000 | Lövqvist et al. ............ 514/338 |
| 6,262,085 B1 * | 7/2001 | Whittle et al. .............. 514/338 |
| 6,262,086 B1 * | 7/2001 | Whittle et al. .............. 514/338 |
| 6,316,020 B1 * | 11/2001 | Whittle et al. .............. 424/439 |
| 6,369,087 B1 * | 4/2002 | Whittle et al. .............. 514/338 |
| 6,444,689 B1 * | 9/2002 | Whittle et al. .............. 514/338 |

OTHER PUBLICATIONS

U.S. patent application No. 09/645,145 to Whittle et al. entitled *Alkoxy Substituted Benzimidazole Compounds, Pharmaceutical Preparations Containing the Same, and Methods of Using the Same*; filed Aug. 24, 2000.

U.S. patent application No. 09/519,976 to Whittle et al. entitled *Alkoxy Substituted Benzimidazole Compounds, Pharmaceutical Preparations Containing the Same, and Methods of Using the Same*; filed Mar. 7, 2000.

U.S. patent application No. 09/629,587 to Whittle et al. entitled *Pharmaceutical Formulations*; filed Jul. 31, 2000.

U.S. patent application No. 09/630,022 to Whittle et al. entitled *Pharmaceutical Unit Dosage Form*; filed Jul. 31, 2000.

U.S. patent application No. 09/628,840 to Whittle et al. entitled *Method of Improving Bioavailability*; filed Jul. 31, 2000.

U.S. patent application No. 09/629,634 to Whittle et al. entitled *Pharmaceutical Unit Dosage Form*; filed Jul. 31, 2000.

"The Mechanism of Action of the Gastric Acid Secretion Inhibitor Omeprazole," *Journal of Medicinal Chemistry* 29:8 1327–1329 (1986).

Allam et al.; "Molecular interaction of tubulin with 1–deaza–7,8–dihydropteridines: a comparative study of enantiomers NSC 613862 (S) and NSC 613863 (R) by Raman and Fourier transform infrared spectroscopy," Int J Biol Macromol 17:1 55–60 (Feb. 1995).

Brändström et al.; "Structure activity relationships of substituted benzimidazoles," *Scandinavian Journal of Gastroenterology* 20:Supplemental 108 15–22 (1985).

Brändström et al.; "Chemical Reactions of Omeprazole and Omeprazole Analogues. I. A Survey of the Chemical Transformations of Omeprazole and its Analogues," *Acta Chemica Scandinavica* 43:536–548 (1989).

Brändström et al.; "Chemical Reactions of Omeprazole and Omeprazole Analogues. II. Kinetics of the Reaction of Omeprazole in the Presence of 2–Mercaptoethanol," *Acta Chemica Scandinavica* 43:549–568 (1989).

Brändström et al.; "Chemical Reactions of Omeprazole and Omeprazole Analogues. III. Protolytic Behaviour of Compounds in the Omeprazole System," *Acta Chemica Scandinavica* 43:569–576 (1989).

Brändström et al.; "Chemical Reactions of Omeprazole and Omeprazole Analogues. IV. Reactions of Compounds of the Omeprazole System with 2–Mercaptoethanol," *Acta Chemica Scandinavica* 43:577–586 (1989).

Brändström et al.; "Chemical Reactions of Omeprazole and Omeprazole Analogues. V. The Reaction of N–Alkylated Derivatives of Omeprazole Analogues with 2–Mercaptoethanol," *Acta Chemica Scandinavica* 43:587–594 (1989).

Brändström et al.; "Chemical Reactions of Omeprazole and Omeprazole Analogues. VI. The Reactions of Omeprazole in the Absence of 2–Mercaptoethanol," *Acta Chemica Scandinavica* 43:595–611 (1989).

By et al.; "Fourier transform infrared/Raman differentiation and characterization of cis– and trans–2,5–dimethoxy–4, beta–dimethyl–beta–nitrostyrenes: precursors to the street drug STP," J Forensic Sci 37:2 503–512 (Mar. 1992).

By et al.; "4–Hydroxybenzazoles: Preparation and Antibacterial Activities," *J. Pharm. and Pharmacol* 8:661–665 (1956).

Clissold et al.; "Omeprazole A Preliminary Review of its Pharmacodynamic and Pharmacokinetic Properties, and Therapeutic Potential in Peptic Ulcer Disease and Zollinger–Ellison Syndrome," *Drugs* 32:15–47 (1986).

Dluhy et al.; "Infrared characterization of conformational differences in the lamellar phases of 1,3–dipalmitoyl–sn–glycero–2–phosphocholine," Biochim Biophys Acta 821:3 437–444 (Dec. 19, 1985).

Erlandsson; "Resolution of the enantiomers of omeprazole and some of its analogues by liquid chromatography on a trisphenylcarbomoylcellulose–based stationary phase. The effect of the enantiomers of omeprazole on gastric glands," *Journal of Chromatography* 532:305–319 (1990).

Lindberg et al.; "Structure–activity relationships of omeprazole analogues and their mechanism of action," *TIPS* 8:399–402 (Oct. 1987).

Maier et al.; "Diphenylethanediamine (DPEDA) Derivatives as Chiral Selectors: IV. A Comparison of 3,5–Dinitrobenzoylated (S,S)– and (S,R)–DPEDA–Derived Chiral Stationary Phases with Pirkle's Standard (R)–Phenylglycine–Derived Phase in Normal Phase HPLC," *Chirality* 6:116–128 (1994).

Marle et al.; "Separation of enantiomers using cellulase (CBH I) silica as a chiral stationary phase," *Journal of Chromatography* 582:233–248 (1991).

Marle et al.; "Chiral stationary phases based on intact and fragmented cellobiohydrolase I immobilized on silica," *Journal of Chromatography* 648:333–347 (1993).

Matysik et al.; "Raman spectroscopic analysis of isomers of biliverdin dimethyl ester," J Pharm Biomed Anal 15:9–10 1319–1324 (Jun. 1997).

Ohishi et al.; "Structure of 5–Methoxy–2–{[4–methoxy–3, 5–dimethyl–2–pyridinyl)methyl]sulfinyl}–1H–benzimidazole (Omeprazole)," *Acta Cryst.* C45:1921–1923 (1989).

Rudiger et al.; "Reconstitution of bacteriorhodopsin from apoprotein and retinal studied by Fourier–transform infrared spectroscopy," Biochemistry 36:16 4867–4874 (Apr. 22, 1997).

Rudolph et al.; "Phase characteristics of positional isomers of 1,2–di(heptacosadiynoyl)–sn–glycero–3–phosphocholine; tubule–forming phosphatidylcholines," Biochim Biophys Acta 943:3 454–462 (Sep. 1, 1988).

Sachs et al.; "Gastric H,K–ATPase as Therapeutic Target," *Ann. Rev. Pharmacol. Toxicol.* 28:269–284 (1988).

Uray et al.; "Diphenylethanediamine derivatives as chiral selectors VIII. Influence of the second amido function on the high–performance liquid chromatographic enantioseparation characteristics of (N–3,5–dinitrobenzoyl)–diphenylethanediamine based chiral stationary phases," *Journal of Chromatography A* 799:1+2 67–81 (Mar. 1998).

von Unge et al.; "Stereochemical assignment of the enantiomers of omeprazole from X–ray analysis of a fenchyloxymethyl derivative of (+)–(R)–omeprazole," *Tetrahedron: Asymmetry* 8:12 1967–1970 (1997).

* cited by examiner

FT-RAMAN SPECTROSCOPIC MEASUREMENT

CROSS-REFERENCE TO RELATED APPLICATIONS

The instant application claims priority to U.S. Provisional Application Serial No. 60/150,878, filed Aug. 26, 1999, the disclosure of which is incorporated herein by reference in its entirety.

FIELD OF THE INVENTION

The present invention relates to mathematically determining isomeric proportions within a chemical composition using a Fourier Transform Raman Spectrometer (FT-Raman) to create a standard curve.

BACKGROUND OF THE INVENTION

Fourier Transform Raman Spectroscopy (FT-Raman) characterizes chemical compounds by using laser light excitation, which produces elastically scattered light (Rayleigh) and in elastically scattered light (Raman). Filtering within the FT-Raman eliminates intense Rayleigh scattering, which is typically in the range of $10^8$ times stronger than the Raman scattering. After passing the filter, a grating disperses the light onto a detector to generate a spectrum. This spectrum provides molecular bonding information about the sample. Light loses energy to molecular vibration, inducing Raman shift, of $v_{laser} - v_{scattered} = v_{Raman}$. Frequency range of the FT-Raman ranges from about 4000 $cm^{-1}$ to about 50 $cm^{-1}$ corrected for the Raman laser frequency. Raman use has been disclosed in such patents as U.S. Pat. No. 2,527,121 to Dudenbostel, Jr., the disclosure of which is herein incorporated by reference.

Various compounds used in inhibiting gastric acid secretion are known in the art and include a class of benzimidazole-substituted compounds, one of which is omeprazole. Omeprazole is currently used as the active pharmaceutical ingredient(API) in the commercial United States formulation PRILOSEC® (manufactured by Merck and Company of Raway, N.J.). In particular, U.S. Pat. No. 4,255,431 (herein referred to as the '431 patent) proposes such benzimidazole-substituted compounds generally described by the formula (III) in the '431 patent that allegedly encompasses omeprazole. Various methods of making these compounds are proposed in the '431 patent. The disclosure of U.S. Pat. No. 4,255,431 is herein incorporated by reference for the purpose of preparing omeprazole, and pharmaceutical formulations thereof.

Problematic with the '431 patent is that the omeprazole compound has been understood to contain a singular 5-OCH$_3$ structure on the benzimidazole moiety (see Tables 1 and 2, at Ex. 23 of the '431 patent). Standard references also identify omeprazole as exclusively containing this "5-methoxy" structure, including "The United States Pharmacopeia, The National Formulary",USP 24, NF 19 (Jan. 1, 2000) at page 1217; Physicians' Desk Reference®, 51 Edition 1997 at page 516; and "The Merck Index", Twelfth Edition 1996 at page 1174 at entry 6977, the disclosures of these references are herein incorporated by reference. Correct determination of the structure of the omeprazole (API or drug product) is necessary for proper pharmaceutical use. A recognition of the omeprazole compound as having various or differing isomeric forms in the solid state has heretofore been unrealized, as well as any determination of the amounts of individual isomeric mixtures.

SUMMARY OF THE INVENTION

The present invention relates to mathematically determining isomeric proportions within a chemical composition, specifically for an omeprazole composition having a fixed ratio of the 5-methoxy and 6-methoxy isomeric chemical components. The 5-methoxy and 6-methoxy ratio is determined with FT-Raman Spectroscopy to measure, monitor and/or control proper isomeric ratio(s) within omeprazole.

DETAILED DESCRIPTION OF THE PREFERRED EMBODIMENTS

The present invention relates to mathematically determining isomeric proportions within a chemical composition, specifically for an omeprazole composition having a fixed ratio of the 5-methoxy and 6-methoxy (collectively referred to herein as "5/6-methoxy") isomeric chemical components. The relative amounts of the 5-methoxy and 6-methoxy isomeric components in omeprazole are determined through measurement of, either or both, 5/6-methoxy isomeric levels of an omeprazole composition relative to a standard curve. A Fourier Transform Raman Spectrometer (FT-Raman) is used to characterize the chemical structure of the omeprazole sample, which shows prominent 5/6-methoxy peaks in the range of from about 1345 $cm^{-1}$ to about 1360 $cm^{-1}$ for the 6-methoxy and from about 1360 cm.$^{-1}$ to about 1370 $cm^{-1}$ for the 5-methoxy.

Previously, omeprazole was understood to contain only 5-methoxy-2-[[(4-methoxy-3,5-dimethyl-2-pyridinyl)methyl]sulfinyl]-1H-benzimidazole) (referred to herein as "5-methoxy") without containing any 6-methoxy-2-[[(4-methoxy-3,5-dimethyl-2-pyridinyl)methyl]sulfinyl]-1H-benzimidazole (referred herein as "6-methoxy"), with the structures shown below:

5-Methoxy

6-Methoxy

It has been unexpectedly discovered that omeprazole comprises an isomeric mixture of 5-methoxy and 6-methoxy isomers of 7:93±2%. Heretofore, variations of this ratio have not been known, up to and including a pure 6-methoxy composition of omeprazole. Ratios of the 5/6-methoxy are fixed with the method described herein for a given sample. Isomeric mixtures of omeprazole range from about 0% to about 100% 5-methoxy and from about 0% to about 100% 6-methoxy, such that the sum of the two isomers equals 100%. Other preferred ranges are identified herein. Fixing the ratio of the 5/6-methoxy isomers within omeprazole, API or drug product, allows determination and/or formulation of the proper ratio of the 5/6-methoxy isomers for use in mammals, either for human or animal use.

The 5-methoxy isomer of omeprazole is significantly less stable than the 6-methoxy isomer, and accordingly, degradation of the 6-methoxy isomer generally occurs slower than the 5-methoxy isomer. Degradation products of the 5-methoxy and, to a much lesser extent the 6-methoxy, isomer creates an adverse environment for the stability of the remaining omeprazole (either 5-methoxy or 6-methoxy). This adverse environment created by the degradation products precipitously degrades the remaining omeprazole once the amount of degradation products reaches a certain level, such as from about 5% or more. As such, proper control of the degradation of omeprazole becomes dependant on fixing the amount of the 5/6-methoxy isomeric ratio within the omeprazole. Accordingly, the amount of 6-methoxy must be fixed within an omeprazole sample to provide reliable stability characteristics.

The ratio of the 5/6-methoxy isomers of omeprazole is quantified within the present invention using a Raman spectroscopic method that was developed using an FT-Raman spectrometer (Nicolet Nexus 670 with a Raman accessory, 1064 nm laser, and step and repeat sampling device; Nicolet Instruments Corp. of Madison, Wis.). Standards are prepared to establish a standard curve using the FT-Raman. The standard curve is used to evaluate unknown samples of omeprazole. A plurality of standards is required for creating the standard curve, and generally the error of the standard curve is decreased with the greater number of standards used for standard curve calculation. The error within a standard curve may be appreciated by those skilled in the art from the number of standards used, the deviation and/or variation between standards and within a given standard, the 5/6-methoxy ratio difference between standards, the rated resolution of the FT-Raman spectrometer used, and other factors reasonably expected to vary interpretative data in light of the disclosure herein. Generally, a minimum of 4 standards are prepared and used to ensure reliability, with from about 5 or more standard used to more reliably reduce error.

The FT-Raman is used to create the standard curve of the omeprazole composition. Multiple scans and/or replicates may be used and averaged to improve accuracy, such as from about 15 scans or more, more preferably from about 200 scans to about 800 scans, and most preferably from about 400 scans to about 600 scans, or from about 5 replicates or more, more preferably from about 10 replicates to about 50 replicates, and most preferably from about 15 replicates to about 30 replicates, with the determination for the proper number of scans and/or replicates determinable by those skilled in the art. Applicants have surprisingly found that omeprazole varies in amounts, Omeprazole is commonly used as an active pharmaceutical ingredient, for use within a drug product. However prior to the present invention, proper determination and quantification of the 5-methoxy and 6-methoxy isomeric components of omeprazole have been unknown. Theoretically omeprazole may range from zero percent (0%) to one hundred percent (100%) 6-methoxy, with the corresponding percentage of 5-methoxy of from 100% to 0%.

Figure 1:
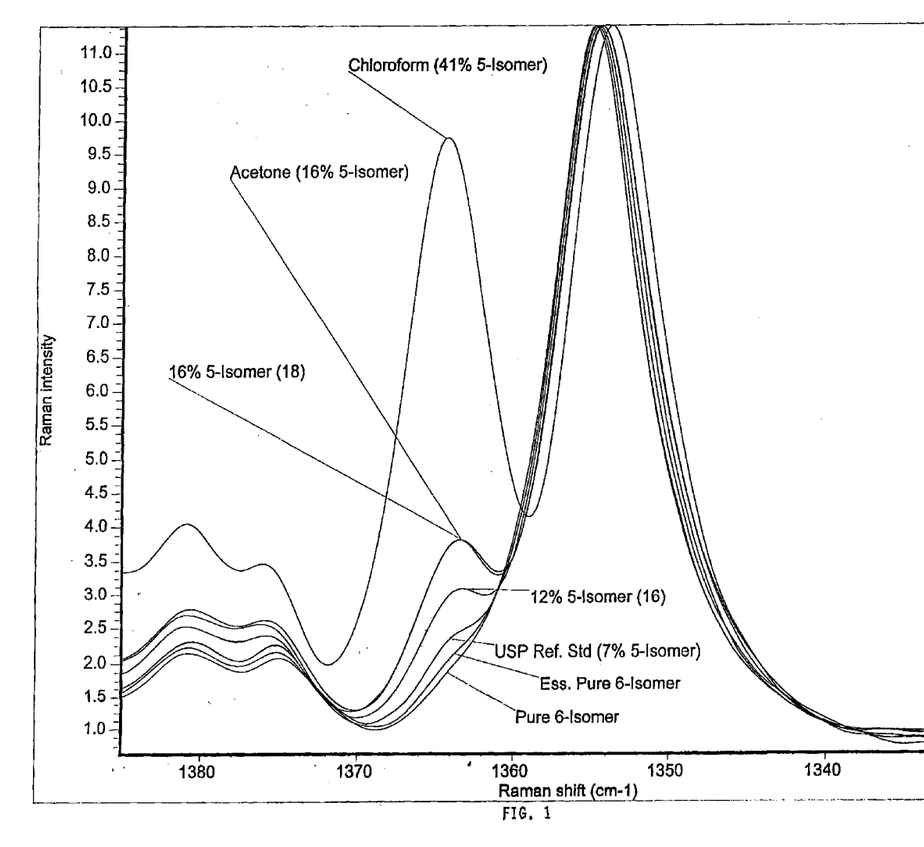
FIG. 1 shows a FT-Raman spectrum between 1330 $cm^{-1}$ and 1390 $cm^{-1}$ for omeprazole compositions of pure 6-methoxy, essentially pure 6-methoxy, 93% 6-methoxy, 88% 6-methoxy (2 spectra), 84% 6-methoxy, and 59% 6-methoxy for the present invention.

As seen in FIG. 1, with the creation of the FT-Raman curve, the isomeric peaks of the 5-methoxy and 6-methoxy isomers of the omeprazole composition are identified. These peaks exist at approximately 1354 $cm^{-1}$ for the 6-methoxy isomeric unit and approximately 1365 $cm^{-1}$ for the 5-methoxy isomeric unit. Measurements are taken of the area under either or both of the two isomeric curves, i.e., 5-methoxy and/or 6-methoxy isomers. Overlap occurs between the 5-methoxy and 6-methoxy isomeric curves which interferes with the direct accurate measurement for the determination of the amounts of the 5-methoxy and 6-methoxy isomers within the omeprazole sample. Accordingly, peak deconvolution algorithms are used to resolve the overlap and permit more accurate measurement.

Additionally, the 5-methoxy and 6-methoxy isomeric peaks of the omeprazole composition were measured relative to "signature peaks" of predominantly non-isomeric components of the omeprazole composition. Peaks from predominantly non-isomeric components of the omeprazole composition were used to provide the relative degree of emissivity or relative intensity between the 5-methoxy and 6-methoxy peaks. Measurements found that the 5-methoxy and 6-methoxy correlated to one another at approximately 1:1. The predominantly non-isomeric components included measurements of one or more curves such as the peaks at 1587 $cm^{-1}$, 1627 $cm^{-1}$, 1185 $cm^{-1}$, and other identifiable peaks from predominantly non-isomeric components of the omeprazole, as determinable by those skilled in the art particularly in light of noise, excipient interference and/or other chemical additive interference for a particular FT-Raman device and/or omeprazole composition over a given region of the spectrum. Preferably,the peak at approximately 1587 $cm^{-1}$ is used. Multiple peaks may be measured and averaged together.

After creation of the standard curve, unknown isomeric omeprazole compositions were measured and compared to provide the ratio of isomeric components of the 5/6-methoxy in the sample.

Preparation of Standards

Seven standards were prepared using the methods set forth in Standards 1-6 below, plus a commercially available sample of omeprazole purchased from the United States Pharmacopia (USP). Preparation of standards was done to maximize the variance of the 5/6-methoxy ratio between standards. In addition to the USP standard (Standard no. 3, approximately 7% 5-methoxy), a low 5-methoxy isomeric concentration (Standard no. 2, approximately 4–5% 5-methoxy), an extremely low 5-methoxy isomer concentration (preferably in pure form, i.e., 100% 6-methoxy) (Standard no. 1, approximately 0% 5-methoxy), at least one high concentration 5-methoxy isomer concentration (Standard no. 7, approximately 40–50% 5-methoxy), and two or more standards distributed over the range from about 5% to about 30% 5-methoxy (Standard nos. 4–6, approximately 12, 16 and 16.5% 5-methoxy, respectively). To establish the standard curve, each standard was run with at least triplicate preparations with at least 15 replicates for each standard preparation and at least 500 scans per replicate, using a resolution of 2 $cm^{-1}$, using the step and repeat sampling device in the continuous mode with instrument parameters set to generate an acceptable signal to noise (S/N).

Standard 1: Preparation of Pure 6-methoxy

To a 1000 mL glass bottle having a screw cap having about 300 mL of methanol was added 1.93 g of sodium hydroxide pellets. The solution was stirred until such pellets dissolved, and omeprazole API was added until a heavy suspension was formed. The solution was capped and allowed to sit, at ambient temperature, for four days, then filtered using vacuum filtration and a paper filter. The resulting solid was washed with three, 50 mL portions of methanol, then placed in a vacuum oven to dry at ambient temperature. The compound was removed after drying for 24 hours, and the purity confirmed by FT-Raman spectroscopy. All samples are shown to be pure 6-methoxy by Raman spectroscopy.

Standard 2: Preparation of Essentially Pure 6-methoxy (4%-6% 5-methoxy)

Approximately 850 mL of methanol was placed in a 1 liter glass bottle with a screw cap. The solution was saturated by dissolving approximately 10.5 g of 5/6-methoxy, and the resulting solution was stirred. Once the solution was saturated, an additional 17 g of 5/6-methoxy was added to the saturated solution to create a suspension. The cap was sealed and the saturated suspension was allowed to stir and equilibrate for about four days.

After four days, the suspension was filtered through a paper filter and then washed with a small amount of methanol. The supernatant was returned to the 1 liter glass bottle and an additional 10 g of 5/6-methoxy was added to the saturated solution. The procedure was repeated to create additional sample. All samples are shown to be essentially pure 6-methoxy by Raman spectroscopy. This procedure has also been successfully carried out using ethanol.

Standard 3: United States Pharmacopia (7%–8% 5-methoxy)

Commercially available sample of omeprazole purchased from the United States Pharmacopia (USP).

Standard 4: Preparation of 5/6-methoxy (11%–13% 5-methoxy)

To a 50 mL beaker was added about 1 g of 5/6-methoxy to 30 mL of methylene chloride. Additional 5/6-methoxy was added to the resulting solution until a suspension of the material was formed. The solution was stirred for approximately 10 minutes, and then filtered through a 0.45 m Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the compound was confirmed by single crystal x-ray diffraction indicating the resulting material to contain between about 81 and 86 percent (w/w) of the 6-methoxy and between about 14 and 19 percent (w/w) of 5-methoxy. Deconvolution of Raman spectroscopy showed the resulting material to contain approximately 88 percent (w/w) of the 6-methoxy and approximately 12 percent (w/w) of 5-methoxy.

Standard 5: Preparation of 5/6-methoxy (15%–17% 5-methoxy)

To a 50 mL beaker was added about 1 g of 5/6-methoxy to 30 mL of acetone. Additional 5/6-methoxy was added to the resulting solution until a suspension of the material was formed. The solution was stirred for approximately 10 minutes, and then filtered through a 0.45 m Poly(tetrafluoroethylene)(PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the compound was confirmed by single crystal x-ray diffraction indicating the resulting material to contain between about 79 and 82 percent (w/w) of the 6-methoxy and between about 18 and 21 percent (w/w) of 5-methoxy. Deconvolution of Raman spectroscopy showed the resulting material to contain approximately 84 percent (w/w) of the 6-methoxy and approximately 16 percent (w/w) of 5-methoxy.

Standard 6: Preparation of 5/6-methoxy (15%–17% 5-methoxy)

To a 50 mL beaker was added about 1 g of 5/6-methoxy to 30 mL of ethanol containing 1 mL of ammonium hydroxide. Additional 5/6-methoxy was added to the resulting solution until a suspension of the material was formed. The solution was stirred for approximately 10 minutes, and then filtered through a 0.45 m Poly(tetrafluoroethylene) (PTFE) or Nylon filter. The resulting saturated solution was placed in a shallow petri dish, covered and stored under refrigerated conditions (approximately 5° C.) until crystals formed (between 2–6 days). The identity of the compound was confirmed by single crystal x-ray diffraction indicating the resulting material to contain between about 85 and 88 percent (w/w) of the 6-methoxy and between about 12 and 15 percent (w/w) of 5-methoxy. Deconvolution of Raman spectroscopy showed the resulting material to contain approximately 84 percent (w/w of the 6-methoxy and approximately 16 percent (w/w) of 5-methoxy.

Standard 7: Preparation of 5/6-methoxy (40%–50% 5-methoxy)

To a 50 mL beaker was added about 1 g of 5/6-methoxy to 30 mL of chloroform. Additional 5/6-methoxy was added to the resulting solution until a suspension of the material was formed. The solution was stirred for approximately 10 minutes, and then filtered through a 0.45 m Poly(tetrafluoroethylene)(PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the compound was confirmed by single crystal x-ray diffraction indicating the resulting material to contain between about 50 and 60 percent (w/w) of the 6-methoxy and between about 40 and 50 percent (w/w) of 5-methoxy. Deconvolution of Raman spectroscopy showed the resulting material to contain approximately 58 percent (w/w) of the 6-methoxy and approximately 42 percent (w/w) of 5-methoxy.

API 5/6-methoxy Determination

Raman spectra were created for each selected standard as specified. Except for the pure 6-methoxy isomer standard, a deconvolution algorithm was used to deconvolute the peak areas of the peaks at approximately 1365 $cm^{-1}$ for the 5-methoxy isomer and approximately 1354 $cm^{-1}$ for the 6-methoxy isomer. The pure 6-methoxy showed a single peak at about 1354 $cm^{-1}$, and as such the percent 6-methoxy was set at a concentration of 100 percent. A software program capable of analyzing Raman spectra in deconvolution algorithm format such as, for example, Nicolet's TQ Analyst™, was used to generate an area percentage of the 5-methoxy relative to the total area of the 5/6-methoxy isomer of each non-pure 6-methoxy standard for the 5/6-methoxy isomer. The area percent was visually checked against the curve to ensure that the measured amounts rationally compared with the curve. The standard deviation for each set of replicates for a standard was less than about 0.7%, and the average standard deviation for the average of all runs and replicates of a given standard was less than about 0.7%.

Figure 2:
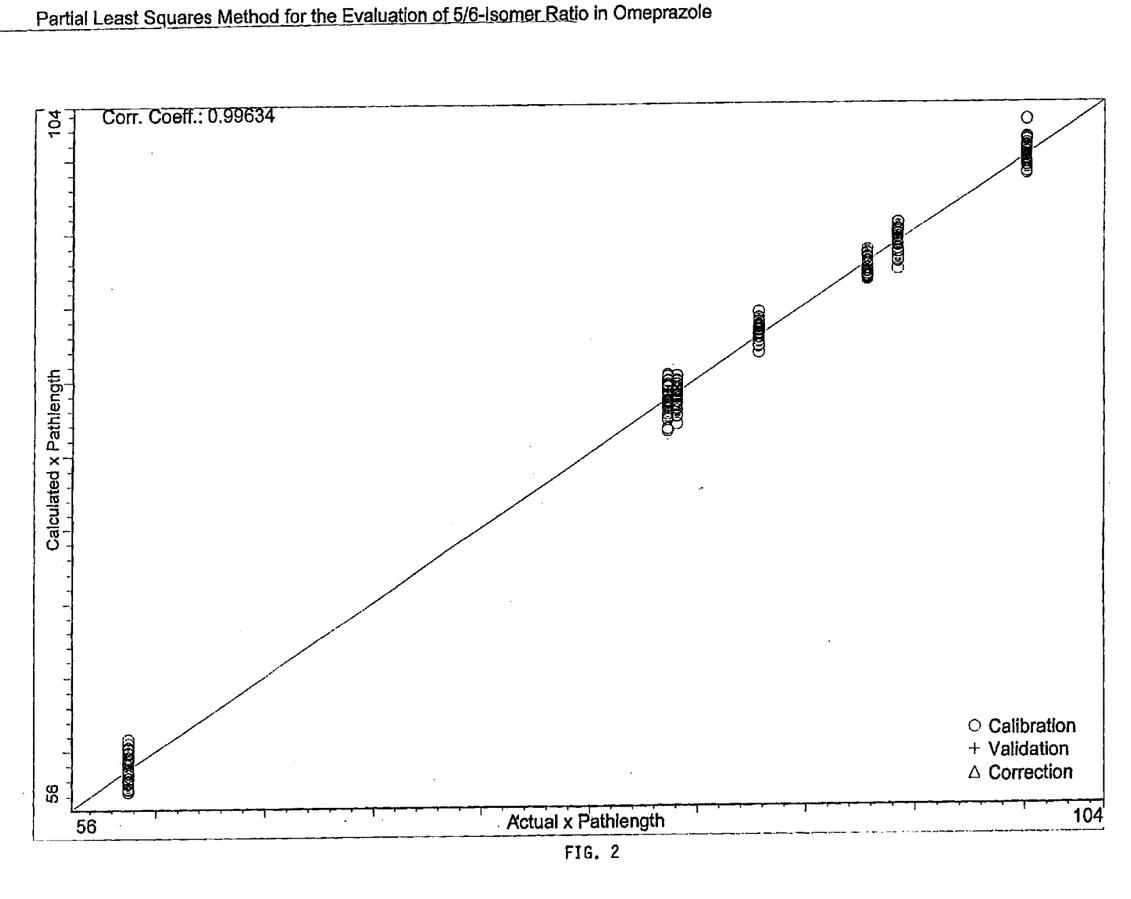
FIG. 2 depicts a regression analysis of the average deconvolution of each standard and calculated partial least squares analysis of standard spectra; and, FIG. 3 shows the FT-Raman graph for pure 6-methoxy, 88% 6-methoxy, mannitol and Prilosec®, respectively.
Figure 3:
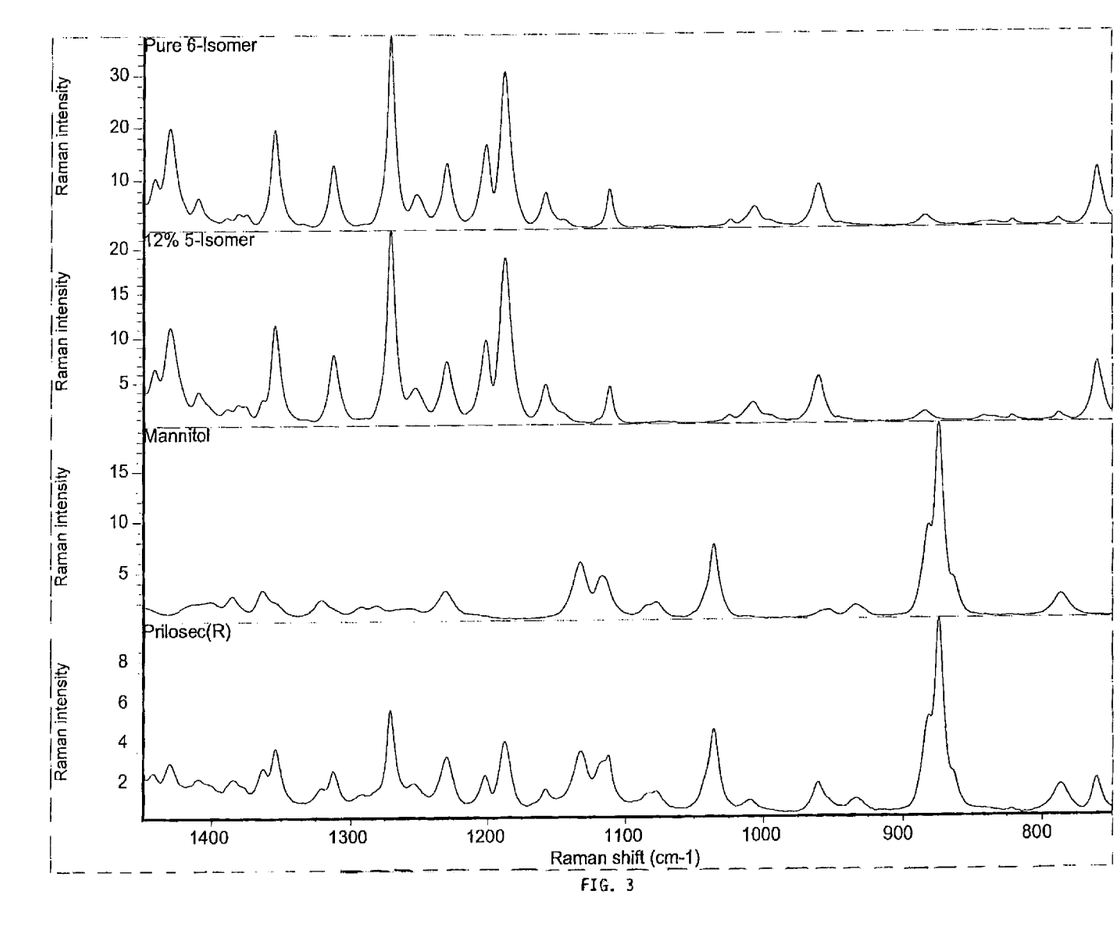

A software program capable of analyzing Raman spectra in a partial least squares format such as, for example, Nicolet's TQ Analys™, was used to generate a standard curve using the average determined percent 6-methoxy isomervalues and the spectrum of a given standard, and to assure accuracy, the correlation coefficients should be at or above about 0.98 among all standards for a given method. FIG. 2 depicts a regression analysis of the average deconvolution and the calculated partial least squares analysis of standard spectrum.

Each omeprazole sample was then analyzed using the method described for establishing the standards, except at least 5 replicates per sample preparation were used, and at least 100 scans per replicate with at least triplicate preparations per sample were used. Using the above-referenced partial least squares analysis, the percent 6-methoxy isomer, and thus the percent 5-methoxy isomer was determined for each scan and the average of the 15 spectra was calculated. The standard deviation (SD) for each scan set of replicates was less than about 1.0%, and the average standard deviation of all runs and replicates of a given sample was less than about 1.0%. High standard deviation values are an indication of variability which may be caused by small amounts of sample burning. When burning is suspected, the preparation should be repeated.

Using the methods taught above, results from establishing the standard curve are as follows:

| Standard | % 5-methoxy | % 6-methoxy | Standard Deviation (SD) |
|---|---|---|---|
| Standard 1 | 0.000 | 100.000 | 0 |
| Standard 2 | 5.875 | 94.125 | 0.338 |
| Standard 3 (USP) | 7.250 | 92.750 | 0.556 |
| Standard 4 | 12.246 | 87.754 | 0.505 |
| Standard 5 | 16.005 | 83.995 | 0.501 |
| Standard 6 | 16.413 | 83.587 | 0.597 |
| Standard 7 | 41.673 | 58.327 | 0.328 |

Using the API quantitative method taught above, 3 lots of omeprazole API (commercial API lots from Merck and Company, Raway, N.J.) were analyzed. Results are as follows:

| Sample/Lot | % 5-methoxy | % 6-methoxy | Standard Deviation (SD) |
|---|---|---|---|
| 01 | 7.50 | 92.50 | 0.77 |
| 02 | 8.02 | 91.98 | 0.56 |
| 03 | 7.61 | 93.39 | 0.81 |

Results from these data through the above-described quantitative method confirmed that the compound known as omeprazole is not 5-methoxy as previously designated (e.g., USP standard for omeprazole and 3 lots of omeprazole API from the sole United States manufacturer of omeprazole), but rather a 5/6-methoxy in a tightly defined ratio of about 7:93±from about 2% of the 5-methoxy isomer and 6-methoxy isomer, respectively.

As seen in FIG. 1, a shift in frequency the 5-methoxy and 6-methoxy curves also is detectable in proportion to the ratio amount of the two isomeric components, ranging between 1353 $cm^{-1}$ for pure 6-methoxy to 1354 $cm^{-1}$ for 40% 5-methoxy. The frequency of the maxima of individual peaks and minima of the valleys shift to high or lower wave numbers depending on the relative percentage of 5/6-methoxy in the standards. Correlations of many of the prominent peaks were examined between standards with consistent results. However, the small variations in the wave numbers between sample and standards allowed for relatively large errors in calculations. With increased accuracy of the detecting FT-Raman, this frequency shift becomes useful in quantifying the 5/6-methoxy ratio.

API and Drug Product 5/6-methoxy Determination

An additional method for quantifying the ratio of the 5/6-methoxy isomers of omeprazole API, albeit less precise than the quantitative FT-Raman method previously described herein, as well as ratio of the 5/6-methoxy isomers in omeprazole drug product was developed. This method also used an FT-Raman spectrometer (Nicolet Nexus 670 with a Raman accessory, 1064 nm laser, and step and repeat sampling device). This method, too, is conducted in three stages: preparation of standards, establishing a standard curve, and analysis of samples. Typically a minimum of 4 to 5 standards are prepared.

The present FT-Raman method for API and drug product analysis uses the same method set forth above, including preferred aspects, as the method set forth for the more quantitative API method relative to the number of preparations and scans per replicate of each standard, resolution, sampling device, deconvolution of standard peaks, determination of peak area, and standard deviation for each set of replicates and the average of all runs and replicates of a given standard.

Rather than a partial least squares analysis, however, a software program capable of analyzing Raman spectra in a corrected classical least squares format, for example, Nicolet's TQ Analyst™, was used to generate a standard curve using the determined percent 6-methoxy isomer values and the spectrum of a given standard. The method is performed by a ratio of a main omeprazole band (such as, for example, approximately 1627 $cm^{-1}$) to a second suitable omeprazole band (such as, for example, the peak at about 1587 $cm^{-1}$). In the event the presence and magnitude of the matrices from pharmaceutical excipients in drug product interfere with the resolution of the peak related to the 6-methoxy isomer and/or the preferred internal omeprazole band, other sets of bands, such as 1587 $cm^{-1}$ and 1201 $cm^{-1}$, respectively, and 1185 $cm^{-1}$ and 1512 $cm^{-1}$, respectively, may be used. Correlation coefficients were at or above about 0.98 among all standards.

For omeprazole API, each sample is prepared under the same instrument conditions as the standards except it is preferred to use at least 5 replicates per sample preparation and at least 100 scans per replicate. Using the above-referenced corrected classical least squares analysis, the percent 6-methoxy isomer, and thus the percent 5-methoxy isomer, was determined for each scan, and the average of the 15 spectra is calculated. The standard deviation for each set of replicates is less than about 2.0%, and the average standard deviation of all runs and replicates of a given sample was less than about 2.0%.

For omeprazole drug product, capsules and tablets are similarly prepared. For capsules, a sufficient number of capsules, preferably about 5–10 capsules, are opened and the omeprazole beads are emptied into an appropriate container. The container is gently rolled to mix the beads or powder, as appropriate, from the various capsules to provide a generally homogeneous blend. For tablets, a sufficient number of tablets, preferably about 5–10 tablets, are gently ground (vigorous grinding may affect the ratio of 5/6-methoxy isomers in omeprazole), and blended to provide a generally homogeneous blend of the ground material.

Each appropriate composite sample was analyzed under the same instrument conditions as the standards, adjusting to an appropriate laser wattage to compensate for the presence of excipients. For FT-Raman analysis, each sample preparation (the composite from capsules or tablets) was run using at least triplicate preparations with at least 3 replicates and at least 500 scans per replicate. Using a corrected classical least squares analysis, the percent 6-methoxy isomer, and thus the percent 5-methoxy isomer, was determined for each scan, and the average of the 9 spectra was calculated. The standard deviation for each set of replicates was less than about 3.0%, and the average standard deviation of all runs of a given sample was less than about 3.0%.

Although the partial least squares method described above is more accurate than this classical least squares method, the deconvolution of the peaks related to the 5-methoxy and 6-methoxy isomers remains the same for both methods and, thus, the standard curve remains the same. Results from API sample analysis with the classical least squares method showed a slightly lower bias than the results from using the partial least squares method, but the data from the partial least squares analysis of omeprazole API samples confirmed the validity of this method for a generally quantitative method for determining the ratio of 5/6-methoxy isomers in omeprazole drug product (Prilosec®) which is commercially available via prescription. The drug product used in the present classical least squares method was provided by Merck and Company of Raway, N.J.

Results from API analysis using the classical least squares methods are as follows:

| Sample/Lot | % 5-isomer | % 6-isomer | Standard Deviation (SD) |
|---|---|---|---|
| 04 | 6.14 | 93.86 | 0.97 |
| 05 | 6.56 | 93.44 | 1.10 |
| 06 | 6.40 | 93.60 | 1.21 |

When applying this classical least squares analytical method to drug product, it was unexpectedly discovered that the ratio of 5/6-methoxy isomers of omeprazole becomes significantly influenced by a multitude of factors during the preparation of drug product (final pharmaceutical formulations for administration, preferably in unit dosage form).

For the sole omeprazole drug product registered by the U.S. Food and Drug Administration and sold in the United States (Prilosec®), the ratio of the 5/6-methoxy isomers in API typically shifts from a ratio of about 7:93 (±about 2%), for the 5-methoxy and 6-methoxy respectively, to a ratio in drug product of about 14:86 (±from about 3%), for the 5-methoxy and 6-methoxy respectively. Factors such as mechanical manipulation (e.g., grinding or, potentially, aggressive sieving) and, particularly the use of commonly used wet granulation processes during drug product preparation have likely contributed to this significant and unexpected shift.

Various physical conditions may be manipulated during the subjecting step to govern the amount of the 5-methoxy compound, e.g., revolutions per minute (RPM) and length of subjecting step. The subjecting step is preferably carried out from about 350 rpm to about 500 rpm, more preferably from about 350 rpm to about 450 rpm, and most preferably about 450 rpm. A preferred time for carrying out the subjecting step is from about 5 to about 30 minutes, more preferably from about 10 min to about 30 min, and most preferably about 15 minutes. Advantageously, the compounds are not degraded during this operation. The subjecting step may be carried out by various machines that apply appropriate grinding energies to solid materials. Preferably, the machine is a mechanical grinder. One example of a suitable grinder is set forth in U.S. Pat. No. 5,773,173 to Whittle et al., the disclosure of which is incorporated herein by reference in its entirety. It should be appreciated that one may employ embodiments other than those described above for forming such compounds of the present invention in solid state.

Shifts from the more thermodynamically stable compounds, with having a higher percentage of the 6-methoxy isomer (with the pure 6-methoxy isomer being preferred), to the less stable compounds having increasing concentrations of the 5-methoxy isomer in the same composition can affect the stability and dissolution profiles of drug product. Compounds and pharmaceutical formulations of the present invention having such higher percentage of such 6-methoxy isomer provide greater stability.

Using the classical least squares analytical method described above, results for Prilosec® drug product are as follows:

| Prilosec Dosage | % 5-methoxy | % 6-methoxy | Standard Deviation (SD) |
|---|---|---|---|
| 20 mg | 14.7 | 85.3 | 2.3 |
| 20 mg | 14.5 | 85.5 | 2.0 |
| 20 mg | 14.7 | 85.3 | 3.0 |
| 40 mg | 13.2 | 86.8 | 1.6 |
| 40 mg | 12.9 | 87.1 | 0.9 |
| 10 mg | 13.6 | 86.4 | 2.8 |
| 10 mg | 13.3 | 86.7 | 2.4 |

Additionally, a homogeneous dry blend pharmaceutical formulation of the above-referenced omeprazole API from Merck and Company and mannitol was prepared with an equivalent dose of 20 mg per dosage form. Using FT-Raman, as disclosed herein, the ratio of the 5/6-methoxy was determined using the corrected classical least squares method. It was unexpectedly found that the 5/6-methoxy ratio of the dry blend remained the same as the API (approximately 6–7% 5-methoxy and 93–94% 6-methoxy), because the percentage of 5/6-methoxy between Merck and Company API varies from the formulated Prilosec® drug product.

As such, the 5/6-methoxy ratio may be fixed within appropriate pharmaceutical formulations, including compound(s), composition(s) and/or complex(es) of the omeprazole API, at least one metal cation, preferably an alkaline metal cation, especially sodium or magnesium of pharmaceutically acceptable salts, solvates, hydrates, or combinations thereof, and preferably at least one non-aqueous pharmaceutically acceptable carrier, diluent or excipient. Preferably this includes dry blends of the pharmaceutical formulations, which may or may not have varied amounts of 5/6-methoxy ratios as between the API and drug product. Stabilizing agents well known in the pharmaceutical art may be optionally added and blending of the drug product may be moderated to minimize degradation of the omeprazole. Such blended mixture is then directly compressed into a tablet or prepared into other pharmaceutically acceptable dosage forms or, preferably, encapsulated using standard preparation techniques. The final pharmaceutical dosage form, when to be used for oral administration, is then optionally and preferably enterically coated. Such pharmaceutical formulations of the present invention are preferably prepared into unit dosage forms comprising the active ingredient(s) concentrations taught herein, preferably in the range from about 5 mg to about 60 mg per unit dose and at least one aqueous or non-aqueous carrier, diluent, or pharmaceutically acceptable excipient. Dry blends used to maintain essentially the same ratio of the 5/6-methoxy ratio from API to dry product preferably use non-aqueous carriers, diluents, or pharmaceutically acceptable excipients, whereas other dosage forms, including preferred oral dosage forms, use either non-aqueous or aqueous carriers, diluents, or pharmaceutically acceptable excipients. More preferred concentrations range from about 8 mg to about 10 mg, about 16 mg to about 20 mg, and from about 32 mg to about 40 mg per unit dose, while unit doses of about 10 mg, 20 mg, and 40 mg are especially preferred.

Such pharmaceutical formulations, particularly in unit dosage form, are used for treating (including prophyulaxis) the disease states described herein. As such, the present invention further provides methods of treating a subject (e.g., mammals, particularly humans) comprising administering to a subject in need of treatment of gastric acid related diseases and/or disease states, a therapeutically effective, non-toxic amount of the aforementioned pharmaceutical formulations. Preferred compounds and compositions, as active ingredients, unit dosage forms, and dosage strengths are determinable by those skilled in the art in light of the disclosure herein.

The following examples show omeprazole formed in different ratios of the 5/6-methoxy as analytically determined. As such the 5/6-methoxy ratio within omeprazole preparations may be controlled allowing omeprazole to be fixed with a specified ratio of 5-methoxy and 6-methoxy isomeric compounds.

The following are tables (1A and 1B) of exemplary ranges for omeprazole, with Table 1A listing possible ranges of 5/6-methoxy in API and Table 1B listing possible 5/6-methoxy in Drug Product:

TABLE 1A

| (API) | |
|---|---|
| 5-methoxy (%) | 6-methoxy (%) |
| 100 to 0 | 0 to 100 |
| 90 to 0 | 10 to 100 |
| 5 to 0 | 95 to 100 |
| 100 to 9 | 0 to 91 |
| 50 to 0 | 50 to 100 |
| 50 to 10 | 50 to 90 |
| 45 to 12 | 55 to 88 |
| 40 to 18 | 60 to 82 |
| 4 to 1 | 96 to 99 |
| 2 to 0 | (Essentially Pure) 98 to 100 (Pure) |

TABLE 1B

| (Drug Product) | |
|---|---|
| 5-methoxy (%) | 6-methoxy (%) |
| 100 to 0 | 0 to 100 |
| 90 to 0 | 10 to 100 |
| 10 to 0 | 90 to 100 |
| 100 to 15 | 0 to 85 |
| 100 to 20 | 0 to 80 |
| 50 to 15 | 50 to 85 |
| 50 to 20 | 50 to 80 |
| 40 to 18 | 60 to 82 |
| 4 to 1 | 96 to 99 |

TABLE IB-continued

| (Drug Product) | |
|---|---|
| 5-methoxy (%) | 6-methoxy (%) |
| 2 to 0 | (Essentially Pure) 98 to 100 (Pure) |

Especially preferred is API that ranges from about 96% or more and/or about 91% 5 or less 6-methoxy, and drug product ranging from about 89% or more and/or about 83% or less 6-methoxy.

Omeprazole compounds of the present invention, as described herein may be used within the pharmaceutical formulations, such as tablets, pills, powders, elixirs, suspensions, emulsions, solutions, syrups, or capsules, of the omeprazole API, with suitable pharmaceutical formulations determinable by those skilled in the art. Determination of the 5/6-methoxy ratio becomes more difficult with the presence of carriers, diluents, excipients, and/or other compositions used in the omeprazole formulation, such as starches, gum arabic, calcium silicate, microcrystalline cellulose, polyvinylpyrrolidone, cellulose, mannitol, sorbitol, sucrose, dextrose, and the like. Dosage forms are known in the art, such as a unit dosage form, each dosage containing from about 5 mg to about 60 mg, such as from about 8 mg to about 10 mg, about 16 mg to about 20 mg, and about 32 mg to about 40 mg, especially 10 mg, 20 mg, and 40 mg per dosage unit. The term "unit dosage form" refers to physically discrete units, such as capsules or tablets suitable as unitary dosages for human patients and other mammals, with each unit containing a predetermined quantity of one or more active ingredient(s) calculated to produce the desired therapeutic effect, in association with at least one pharmaceutically acceptable carrier, diluent, excipient, or combination thereof. Omeprazole is known forth treating a subject (e.g., mammal, particularly humans) for a number of disorders, particularly for preventing and treating gastric acid related diseases. The amount given to a particular patient may be determined by an attending physician or other qualified person to administer a therapeutically effective amount of the omeprazole.

FIGS. 3A through 3D show the FT-Raman graph for pure 6-methoxy, 88% 6-methoxy, mannitol and Prilosec®, respectively over a range of about 800 $cm^{-1}$ to about 1400 $cm^{-1}$. As seen in FIGS. 3A through 3D, selection of areas of the spectra for analysis is determined relative to the excipients in the drug product.

The foregoing summary, description, examples and drawings of the invention are not intended to be limiting, but are only exemplary of the inventive features which are defined in the claims.

What is claimed is:

1. An omeprazole API composition fixed with a ratio of 5-methoxy and 6 methoxy isomers.

2. The omeprazole API composition of claim 1, fixed with a ratio of from about 4 percent or less 5-methoxy and from about 96 percent or more 6-methoxy.

3. The omeprazole API composition of claim 1, fixed with a ratio of from about 9 percent or more 5-methoxy and from about 91 percent or less 6-methoxy.

4. An omeprazole API composition having a predetermined ratio of 5-methoxy and 6-methoxy.

* * * * *